(12) United States Patent
Crause

(10) Patent No.: US 7,652,173 B2
(45) Date of Patent: Jan. 26, 2010

(54) PRODUCTION OF DETERGENT RANGE ALCOHOLS

(75) Inventor: James Christoffel Crause, Vaalpark (ZA)

(73) Assignee: Sasol Technology (Proprietary) Limited, Sasolburg (ZA)

( * ) Notice: Subject to any disclaimer, the term of this patent is extended or adjusted under 35 U.S.C. 154(b) by 0 days.

(21) Appl. No.: 11/996,885

(22) PCT Filed: Aug. 31, 2006

(86) PCT No.: PCT/IB2006/002379

§ 371 (c)(1), (2), (4) Date: Jun. 12, 2008

(87) PCT Pub. No.: WO2007/029079

PCT Pub. Date: Mar. 15, 2007

(65) Prior Publication Data

US 2009/0054696 A1 Feb. 26, 2009

(30) Foreign Application Priority Data

Aug. 31, 2005 (ZA) .............................. 2005/06978

(51) Int. Cl.
C07C 45/50 (2006.01)
C07C 29/14 (2006.01)
(52) U.S. Cl. ...................... 568/451; 568/880
(58) Field of Classification Search ................. 568/451, 568/700, 880
See application file for complete search history.

(56) References Cited

U.S. PATENT DOCUMENTS 2,763,693 A 9/1956 VanderWoude et al. ...... 260/604
3,087,866 A * 4/1963 Burch .......................... 203/60

FOREIGN PATENT DOCUMENTS

WO WO 2004/080926 A2 9/2004
WO WO 2005/037751 A2 4/2005

OTHER PUBLICATIONS

International Search Report for PCT/IB2006/002379 published Jul. 12, 2007 as WO 2007/029079 A3.

* cited by examiner

Primary Examiner—Sikarl A Witherspoon
(74) Attorney, Agent, or Firm—Brinks Hofer Gilson & Lione

(57) ABSTRACT

This invention relates to a process for the production of alcohols and/or aldehydes. A hydrocarbon feed stream containing paraffins and olefins, typically in which more than 5% by volume of olefin molecules in the hydrocarbon feed stream have a total number of carbon atoms which is different from the total number of carbon atoms of the most abundant two (preferably three) carbon numbers of olefins (by carbon number) in the hydrocarbon stream, is subjected to a hydroformylation reaction in which olefins are converted to alcohols and/or aldehydes. Paraffins in the hydroformylation product are then separated from alcohols and/or aldehydes by azeotropic distillation in an azeotropic distillation column. The invention also relates to a method for separating alcohols/aldehydes from paraffins in a hydrocarbon feed stream in an azeotropic distillation column using a mid-boiling polar entrainer.

22 Claims, 1 Drawing Sheet

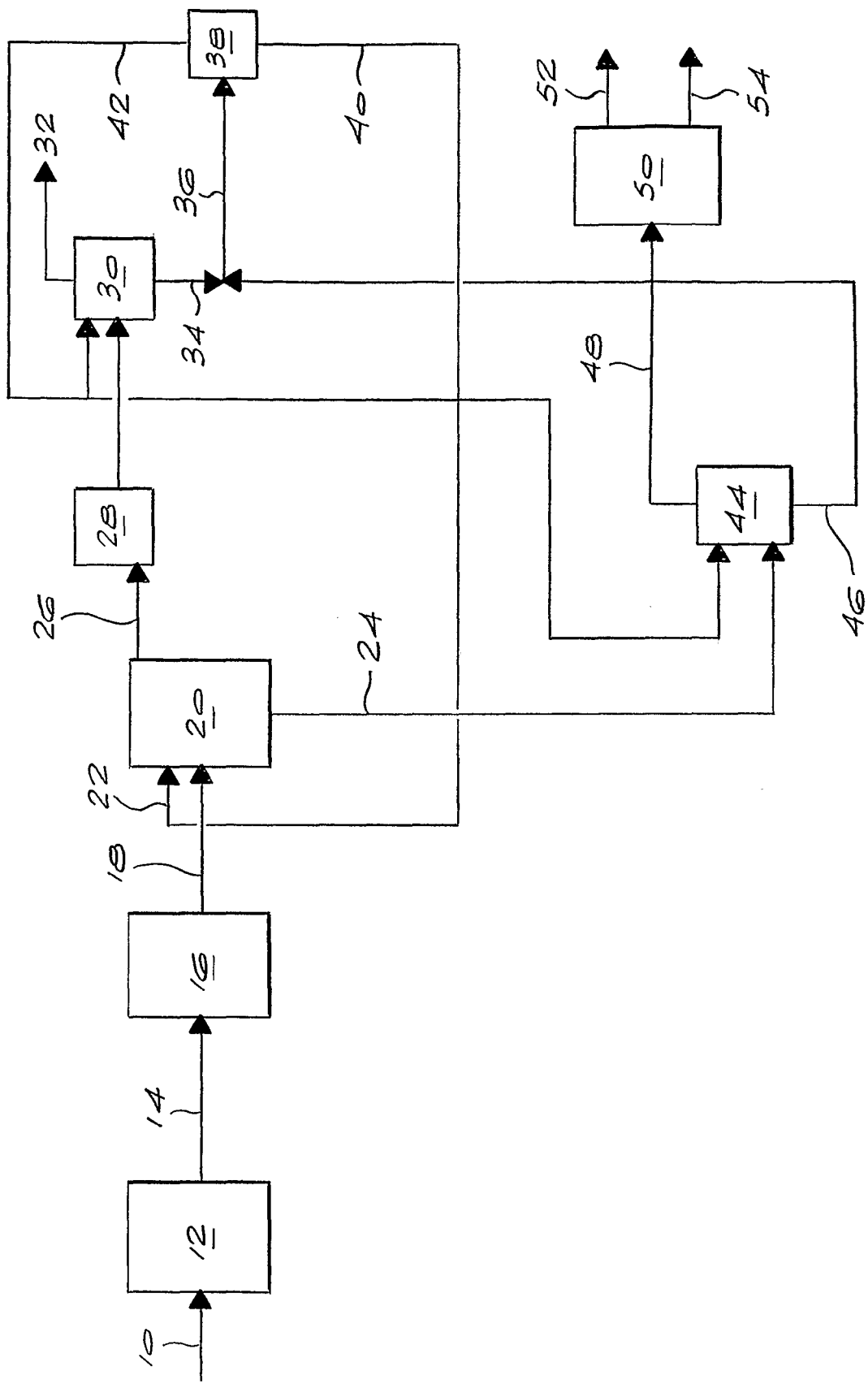

PRODUCTION OF DETERGENT RANGE ALCOHOLS

BACKGROUND OF THE INVENTION

THIS invention relates to a process for the production of alcohols, typically alcohols in the detergent range.

Detergent range alcohols are alcohols, usually in the $C_8$ to $C_{20}$ range, (i.e. from 8 to 20 carbon atoms in the molecules) that are useful in the manufacture of detergents and surfactants.

Detergent alcohols are commercially produced by distilling a desired cut of olefins and paraffins from an olefin rich feed. The olefins are then converted to alcohols by hydroformylation. Paraffins are inert to the hydroformylation reaction and form part of the product. Because it is difficult to separate the alcohols from paraffins in the product where the boiling points of the alcohols and paraffins are similar or overlap, it is an accepted practice to distill a narrow-cut of olefins containing a high concentration of two or less carbon numbered olefins and its associated paraffins. Conversion of the olefins to alcohols increases the boiling points of the olefins relative to the paraffins, thereby facilitating easy separation of the alcohols from the associated paraffins.

Detergent range alcohols may be produced from olefins contained in the condensation product of a high temperature or a low temperature Fischer-Tropsch reaction preferably using an iron based catalyst. Typically a feed stream from such a Fischer-Tropsch reaction consists predominantly of olefins. Sasol commercially operates a process in which the feed stream from the Fischer-Tropsch reaction is fractionated into a stream containing olefins in predominantly the 2C range, which is introduced to a hydroformylation reactor in which the olefins are converted to alcohols and/or aldehydes. The alcohols and/or aldehydes are then separated from paraffins in the stream. The resulting alcohols and/or aldehydes are predominantly in the 2C range.

In order to increase the scale of such a hydroformylation plant, it would be beneficial to use a broader cut of carbon number olefins, for example olefins in the 3C or even 4C range. However, it is well known that the boiling points of the alcohols and/or aldehydes in the hydroformylation product overlaps that of the unreacted parrafins, leading to difficulties in separation of the paraffins from the alcohol and/or aldehyde product.

It is an object of this invention to provide an improved method for the production of alcohols, typically used as detergent precursors.

SUMMARY OF THE INVENTION

According to a first aspect of the invention there is provided a process for the production of alcohols and/or aldehydes, wherein a hydrocarbon feed stream containing paraffins and olefins, typically in which more than 5% by volume of olefin molecules in the hydrocarbon feed stream have a total number of carbon atoms which is different from the total number of carbon atoms of the most abundant two (preferably three) carbon numbers of olefins (by carbon number) in the hydrocarbon stream, is subjected to a hydroformylation reaction in which olefins are converted to alcohols and/or aldehydes and wherein paraffins in the hydroformylation product are separated from alcohols and/or aldehydes by azeotropic distillation in an azeotropic distillation column.

Preferably, the hydrocarbon feed stream contains olefins in which more than 10%, preferably more than 20% by volume, of olefin molecules in the feed have a total number of carbon atoms which is different from the total number of carbon atoms of the most abundant two olefins (by carbon number) in the hydrocarbon stream.

Typically, the hydrocarbon feed stream has an average number of carbon atoms per molecule of from 10 to 18.

Preferably, the hydrocarbon feed stream is derived from a Fischer-Tropsch condensate product.

Typically, oxygenates are removed from the hydrocarbon feed stream, prior to subjecting the stream to the hydroformylation reaction.

The invention also relates to a method for separating alcohols/aldehydes from paraffins in a hydrocarbon feed stream in an azeotropic distillation column, wherein the solvent in the column is a mid-boiling polar entrainer.

The mid-boiling polar entrainer may be Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, Diethanolamine (DEA), or Diethylene glycol (DEG), preferably DEG.

Typically, the entrainer to feed ratio is from 1:05 to 1:3, preferably from 1:1 to 1:2, most preferably 1:1.8.

An overhead stream from the azeotropic distillation column, containing paraffins and mid-boiling polar entrainer, is conveniently supplied to a decanter where a paraffin product is separated from the mid-boiling polar entrainer using a water wash. The mid-boiling polar entrainer may be recycled to the azeotropic distillation column.

A bottoms stream from the azeotropic distillation column is conveniently supplied to a wash column in which an alcohol/aldehyde product is separated from the mid-boiling entrainer using a water wash.

BRIEF DESCRIPTION OF THE DRAWINGS

The drawing is a block diagram of a process according to the invention.

DESCRIPTION OF PREFERRED EMBODIMENTS

This invention relates to the production of detergent range alcohols/aldehydes from a hydrocarbon feedstream. Although a feedstream from a Fischer-Tropsch reaction is described herein, any suitable hydrocarbon feedstream may be used.

A typical Fischer-Tropsch process involves the hydrogenation of CO in the presence of Group VIII metals, and includes, but is not limited to, Fe, Co, Mo, W, Rh, Pt, Pd Os, Ir and Ru. In principle, iron-based, cobalt-based or iron/cobalt-based Fischer-Tropsch catalysts can be used commercially in the Fischer-Tropsch reaction stage. Iron based catalysts are preferred for the present invention since they tend to produce a more olefinic hydrocarbon condensate product. In some embodiments, the iron-based Fischer-Tropsch catalyst may comprise iron and/or iron oxides which have been precipitated or fused. However, iron and/or iron oxides which have been sintered, cemented, or impregnated onto a suitable support may also be used. In some cases the iron based catalyst may contain various levels of promoters, the role of which may be to alter one or more of the activity, the stability, and the selectivity of the final catalyst. Preferred promoters are those influencing the surface area of the reduced iron ('structural promoters'), and these include oxides or metals of Mn, Ti, Mg, Cr, Ca, Si, Al, or Cu or combinations thereof. Preferred promoters for influencing product selectivities are alkali oxides of K and Na. Catalysts for the production of hydrocarbon species by a Fischer Tropsch process are generally known in the art.

The Fischer-Tropsch reaction may be effected in a fixed bed or preferably in a slurry phase reactor for low temperature Fischer-Tropsch applications, or in a fluidized bed reactor for high temperature Fischer-Tropsch applications. The Fischer-Tropsch reaction conditions may include utilizing a reaction temperature of between 190° C. and 340° C., with the actual reaction temperature being largely determined by the desired product spectrum. The products formed from this reaction are gaseous, liquid and optionally waxy hydrocarbons that include, inter alia, olefins and paraffins as well as oxygenates. The carbon number distribution of these products is generally described by the Anderson-Schulz-Flory distribution.

The low temperature Fischer-Tropsch (LTFT) process is a well known process in which synthesis gas, a mixture of gases including carbon monoxide and hydrogen, is reacted over a suitable catalyst to produce a mixture of straight and branched chain hydrocarbons ranging from methane to waxes with molecular masses above 1400 and smaller amounts of oxygenates (relative to high temperature Fischer-Tropsch). The LTFT catalyst may comprise active metals such as iron, cobalt, nickel or ruthenium and the catalyst will normally be a precipitated or supported catalyst. Synthesis gas for the LTFT process may be derived from any carbon containing feedstock such as coal, natural gas, biomass or heavy oil streams. Some reactors for the production of heavier hydrocarbons using the LTFT process are slurry phase or tubular fixed bed reactors, while operating conditions are generally in the range of 180-280° C., in some cases in the 210-260° C. range, and 10-50 bar, in some cases between 20-30 bar. The molar ratio of hydrogen to carbon monoxide in the synthesis gas may be between 0.4 and 3.0, generally between 1.0 and 2.0.

As is the case with the LTFT process, the High Temperature Fischer-Tropsch (HTFT) process also makes use of the FT reaction albeit at a higher process temperature. A typical catalyst for HTFT process is iron based. Fused iron catalysts are best known in the prior art to be used in high temperature Fischer-Tropsch synthesis. Known reactors for the production of heavier hydrocarbons using the HTFT process are the circulating bed system or the fixed fluidized bed system, often referred to in the literature as Synthol processes. These systems operate at temperatures in the range 290-360° C., and typically between 320-350° C., and at pressures between 20-50 bar, in some cases between 20-30 bar. The molar ratio of hydrogen to carbon monoxide in the synthesis gas is essentially between 1.0 and 3.07 generally between 1.5 and 2.5. Generally, recycle streams are applied to increase the hydrogen content in the feed gas to the HTFT reactor to give a molar ratio of hydrogen to carbon dioxide at the reactor inlet of between 3.0 and 6.0 depending on the amount of carbon dioxide in the feed gas. Generally, a stoichiometric ratio, known as the Ribblett ratio $H_2/[2(CO)+3(CO_2)]=1.03$ is used as a target for the feed gas composition. Products from the HTFT process are all in the vapour phase at the reactor exit and are somewhat lighter than those derived from the LTFT process and, as an additional distinction, contain a higher proportion of unsaturated species and oxygenates. The HTFT process is completed through various steps which include the preparation of synthesis gas ($H_2$ and CO) from any carbon containing feedstock such as by natural gas reforming or gasification of coal or other suitable hydrocarbonaceous feedstocks like petroleum based heavy fuel oils or biomass. This is followed by the HTFT conversion of synthesis gas in a reactor system like the Sasol Synthol or the Sasol Advanced Synthol reactor. One of the products from this synthesis is an olefinic distillate, also known as Synthol Light Oil (SLO).

Detailed descriptions of these two FT processes, LTFT and HTFT, may be found in "Fischer-Tropsch Technology", Studies in Surface Science and Catalysis, Vol. 152, Eds. A. P. Steynberg and M. E. Dry, Elsevier, 2004, amongst others.

With reference to the drawing, a HT Fischer-Tropsch reaction, using an iron based catalyst, produces a hydrocarbon condensation product 10 which has been fractionated to provide a hydrocarbon stream containing olefins in which more than 5%, typically more than 10%, preferably more than 20% by volume of olefin molecules in the hydrocarbon stream have a total number of carbon atoms which is different from the total number of carbon atoms of the most abundant two carbon (preferably three) numbers of olefins in the hydrocarbon stream. The fractionated hydrocarbon stream may contain olefins in a 3C range or greater, typically in a 4C range, such as C11-C14 olefins (for example containing approximately 37% C11, 30% C12, 18% C13, and 11% C14 olefins, by volume of the the total olefins in the stream) is introduced to an oxygenate removal step 12 in which oxygenates are removed from the stream. The oxygenate removal step may be achieved by using Liquid-Liquid Extraction (e.g. Acetonitrile/water or methanol/water), dehydration or hydrogenation. From the oxygenate removal step 12, a feed stream 14 containing paraffins and linear olefins is introduced to a hydroformylation reactor 16. In the hydroformylation reactor 16, olefins in the stream are subjected to the "Oxo" process. Hydroformylation (Oxo) processes for the production of oxygenated products, particularly aldehydes and/or alcohols, by the reaction of an olefinic feedstock with carbon monoxide and hydrogen at elevated temperatures and pressures in the presence of hydroformylation catalysts, are well known. The alcohols and/or aldehydes that are produced in these processes generally correspond to the compounds obtained, in the hydroformylation reaction, by the addition of a carbonyl or carbinol group to an olefinically unsaturated carbon atom in the feedstock with simultaneous saturation of the olefin bond. A hydroformylation catalyst is selected according to the particular oxygenated products which are required from a particular olefinic feedstock. Thus, a hydroformylation catalyst may typically include a Group VII metal for example, but not limited to cobalt, rhodium, platinum and palladium. In some embodiments, the metal may be combined with a ligand for example, but not limited to a phosphine and/or phosphite ligand. Examples of such catalysts are triphenyl phosphine ligands used with rhodium, and alkyl phosphine ligands used with cobalt. In the Oxo process, the carbon number of the olefins is increased by 1 and a hydroxyl group is added to form the alcohols/aldehydes.

Hydroformlyation may be conducted as a batch process, continuous process or semi-continuous process. For ligand modified cobalt catalysts, typical hydroformylation temperatures are between 140° C. and 210° C. and preferably between 160° C. and 200° C. Synthesis gas (syngas) composition with respect to the $H_2$:CO ratio may be 1:2-3:1 and preferably about 2:1; syngas pressure may typically be 20-110 bar and preferably 50-90 bar, the molar ratio of ligand to metal may typically be 10:1-1:1 and preferably is 1:1-3:1 and the % metal to olefin by mass may typically be 0.1-1 and preferably is 0.2-0.7.

For ligand modified rhodium catalysts, typical hydroformylation temperatures are between 50° C. and 150° C. and preferably between 80° C. and 130° C. Syngas composition with respect to the $H_2$:CO ratio may be 1:2-3:1 and preferably about 1.1-1.2; syngas pressure may typically be 2-60 bar and preferably 5-30 bar and the % metal to olefin by mass may typically be 0.001-0.1 and preferably is 0.01-0.05.

Paraffins in the feed stream 14 are inert in the Oxo process and pass through the hydroformylation reactor 16 unchanged. In the case of a $C_{11}$-$C_{14}$ feed stream 14, linear alcohols in the $C_{12}$-$C_{15}$ range are formed in the hydroformylation reactor 16, and a stream 18 containing alcohols in the $C_{12}$-$C_{15}$ range and paraffins in the $C_{11}$-$C_{14}$ range exits from the hydroformylation reactor 16.

The separation of alcohols from paraffins in such a wide range as that present in the stream 18 is problematic because of the overlapping boiling points of the heavy paraffins and light alcohols. The boiling points of typical paraffins and alcohols in such a stream are provided below:

Paraffins
n-Undecane (nC11) 196° C.
n-Dodecane (nC12) 216° C.
n-Tridecane (nC13) 235° C.
n-Tetradecane (nC14) 253° C.

Alcohols
Dodecanol (C12OH) 264° C.
Tridecanol (C13OH) 280° C.
Tetradecanol (C14OH) 296° C.
Pentadecanol (C15OH) 310° C.

Although there is a 10° C. difference in the boiling points of the heavy paraffin and the light alcohol, it appears as if the mixture either has a very low relative volatility or forms an azeotrope which makes it difficult or impossible to separate cleanly between the $nC_{14}$ and $C_{12}OH$.

Nevertheless, according to the invention, it has been found that it is possible to effect such a separation by subjecting the stream 18 to azeotropic distillation in an azeotropic distillation column 20. Azeotropic distillation is the use of an additional component that forms an azeotrope with one or more of the feed components to a distillation column and thereby enhancing the relative volatility towards the desired separation.

According to the invention, the azeotropic distillation column 20 is supplied with a mid-boiling polar entrainer 22 at the top of the column 20, and the hydrocarbon stream 18 is supplied to the column 20, mid-way along the column 20. A mid-boiling polar entrainer is a solvent that has a boiling point between the lowest and highest boiling components in the feed to be separated. It is found that mid-boiling entrainers are more effective compared with low-boiling entrainers or high-boiling solvents because the mid-boiling polar entrainer is selected to distribute from a bottoms stream 24 to an overhead stream 26 of the azeotropic distillation column 20, thereby ensuring that the enhancement of relative volatility occurs over the entire column 20.

Candidate entrainers include:
Indole
2-Pyrrolidone
1,6 Hexanediol
N-Aminoethyl-ethanolamine
1,2-Benzenediol
N-methyl pyrrolidone (NMP)
Ethylene carbonate
Propylene carbonate
Diethanolamine (DEA)
Diethylene glycol (DEG)

Of the entrainers identified, DEG is preferred because of its relatively low cost, low toxicity low freezing point and ease of separation from the hydrocarbon and alcohol streams by water extraction.

The addition of DEG leads to the formation of azeotropes with both $C_{14}$ and $C_{12}OH$, but there is a larger boiling point difference of about 13° C. between these new azeotropes which increases the relative volatility between the $C_{14}$ and $C_{12}OH$. The boiling point of DEG is about 245° C. Similar enhancements in relative volatility between $C_{14}$ and $C_{12}OH$ are observed for the other entrainers identified above. Typically, the entrainer 22 to feed 18 ratio is from 1:05 to 1:3, preferably from 1:1 to 1:2, most preferably 1:1.8. According to the process of the invention, the overhead stream 26 from the distillation column 20, containing olefins and mid-boiling polar entrainer, is introduced to a condenser 28 and then to a decanter 30, where a paraffin product 32 is separated in a water wash from the mid-boiling polar entrainer 34. The separated mid-boiling entrainer is then sent via a line 36 to a solvent dryer 38. Dried polar entrainer 40 from the solvent dryer 38 is recycled to the azeotropic distillation column 20. Water 42 from the solvent dryer 38 is conveniently recycled to the Decanter 30. The bottoms stream 24 from the azeotropic distillation column 20, which contains some of the mid-boiling entrainer and alcohols is washed with water in a wash column 44 which is conveniently supplied with water from the water recycle stream 42. A water-phase 46 containing the entrainer is sent to the solvent dryer 38 via the line 36. An alcohol product stream 48 containing $C_{12}$-$C_{15}$ alcohols is obtained from the wash column 44. The stream 48 is then conveniently sent to a splitter column 50 to obtain a first alcohol product 52 in the $C_{12}$-$C_{13}$ range and second alcohol product 54 in the $C_{14}$-$C_{15}$ range.

According to the invention, it is possible to produce an alcohol product through hydroformylation of a feed stream containing olefins and paraffins in which more than 5%, typically more than 10%, preferably more than 20% by volume of olefin molecules in the hydrocarbon stream have a total number of carbon atoms which is different from the total number of carbon atoms of the most abundant two carbon numbers of olefins in the hydrocarbon stream, and still be able to separate paraffins from the alcohols and obtain a useful, pure alcohol product. An advantage of the process of the present invention over the prior art in which the process in which hydroformylation of a hydrocarbon stream in the 2C range is that it is possible to form alcohols in the 3C range or greater in one hydroformylation reactor, whereas in the prior art, two separate reactors and reactions were required.

Although the above description relates to the separation of alcohols from paraffins, the process may also be used for the separation of aldehydes from paraffins.

The invention will now be described with reference to the following non-limiting Example.

A feed stream containing $C_{11}$ to $C_{14}$ paraffins and $C_{12}$ to $C_{15}$ alcohols was introduced to an azeotropic distillation column 20. A mid-boiling entrainer 22 in the form of diethylene glycol (DEG) was introduced to the azeotropic distillation column 20 operating at approx. 15-30 kPa abs. The column is typically operated under vacuum to limit the bottoms temperature to about 200° C.; the preferred pressure range is about 15-30 kPa abs. The optimum number of theoretical stages in this column is approximately 30-35. The DEG flow rate to the azeotropic column was varied together with reboiler duty, reflux ratios of the DEG and hydrocarbon phases and feed point locations to limit the amounts of $C_{14}$ paraffin in the bottoms stream 24 and the $C_{12}$ alcohol in the overhead stream 26 to 1 kg/h respectively. It was found that the DEG should be fed on to the top tray in the column, while the feed is introduced into the middle of the azeotropic column. A DEG:feed ratio of 1:1.8 was required to achieve the desired separation.

A water:feed flow of 1:1 to the decanter 30 was sufficient to reduce the DEG concentration to below 100 ppm in the fuel stream using a two stage extraction column. A water:feed ratio of 6:1 to the product wash column 44 was required to reduce the DEG concentration to below 100 ppm in the alcohol stream 48 using a 5 stage extractor. More stages are used in the product wash column to reduce the required water flow.

Table 1 below shows compositions of the streams 18, 22, 26 and 24 in an Example of the invention.

TABLE 1

| | Stream numbers | | | |
|---|---|---|---|---|
| | 22 | 18 | 26 | 24 |
| | Mass flow, kg/h | | | |
| Components | 10000 | 34621 | 17098 | 27524 |
| | Composition - Mass % | | | |
| Water | 0.50 | 0 | 0.29 | 0 |
| DEG | 99.50 | 0 | 13.13 | 28.00 |
| C11 branched paraffin | 0 | 1.09 | 2.21 | 0 |
| C12 branched paraffin | 0 | 0.86 | 1.75 | 0 |
| C13 branched paraffin | 0 | 1.15 | 2.33 | 0 |
| C14 branched paraffin | 0 | 0.70 | 1.42 | 0 |
| C15 branched paraffin | 0 | 0.20 | 0 | 0.25 |
| C10 normal paraffin | 0 | 0.11 | 0.22 | 0 |
| C11 normal paraffin | 0 | 10.93 | 22.13 | 0 |
| C12 normal paraffin | 0 | 8.70 | 17.61 | 0 |
| C13 normal paraffin | 0 | 4.90 | 9.93 | 0 |
| C14 normal paraffin | 0 | 3.81 | 2.45 | 3.27 |
| C15 normal paraffin | 0 | 0.01 | 0 | 0.01 |
| C10 other paraffin | 0 | 4.68 | 9.47 | 0 |
| C11 other paraffin | 0 | 3.73 | 7.55 | 0 |
| C12 other paraffin | 0 | 2.75 | 5.57 | 0 |
| C13 other paraffin | 0 | 1.71 | 3.46 | 0 |
| C14 other paraffin | 0 | 0.25 | 0.07 | 0.27 |
| C11 branched alcohol | 0 | 0.05 | 0.07 | 0.01 |
| C12 branched alcohol | 0 | 8.32 | 0.32 | 10.27 |
| C13 branched alcohol | 0 | 6.45 | 0 | 8.11 |
| C14 branched alcohol | 0 | 0.22 | 0 | 0.28 |
| C15 branched alcohol | 0 | 0.04 | 0 | 0.05 |
| C16 branched alcohol | 0 | 0 | 0 | 0 |
| C11 linear alcohol | 0 | 0.09 | 0.01 | 0.11 |
| C12 linear alcohol | 0 | 9.58 | 0 | 12.05 |
| C13 linear alcohol | 0 | 7.48 | 0 | 9.41 |
| C14 linear alcohol | 0 | 7.74 | 0 | 9.73 |
| C15 linear alcohol | 0 | 5.91 | 0 | 7.44 |
| C16 linear alcohol | 0 | 0.02 | 0 | 0.02 |
| C11 other alcohol | 0 | 2.59 | 0 | 3.26 |
| C12 other alcohol | 0 | 1.99 | 0 | 2.50 |
| C13 other alcohol | 0 | 2.23 | 0 | 2.81 |
| C14 other alcohol | 0 | 1.60 | 0 | 2.01 |
| C15 other alcohol | 0 | 0.09 | 0 | 0.12 |

Table 2 below shows the conditions in the different columns of this Example.

TABLE 2

| Column | Stages | Reboiler duty/ kW | Condenser duty/kW | Diameter/m |
|---|---|---|---|---|
| Azeotropic 20 | 35 | 3000 | 286 | 2.5 |
| Decanter 30 | 2 | — | — | — |
| Wash column 44 | 5 | — | — | — |
| Solvent dryer 38 | 8 | 6500 | 5500 | 2.2 |
| Splitter 50 | 40 | 5300 | 5500 | 4.5 |

The invention claimed is:

1. A process for the production of alcohols and/or aldehydes, wherein a hydrocarbon feed stream containing paraffins and olefins is subjected to a hydroformylation reaction in which olefins are converted to alcohols and/or aldehydes and wherein paraffins in the hydroformylation product are separated from alcohols and/or aldehydes in the hydroformylation product by azeotropic distillation in an azeotropic distillation column, the azeotropic distillation column containing a solvent which is a mid-boiling polar entrainer, and wherein paraffins are recovered in an overhead stream, and alcohols/aldehydes are recovered in a bottoms stream from the azeotropic distillation column.

2. The process as claimed in claim 1, wherein more than 5% by volume of olefin molecules in the hydrocarbon stream have a total number of carbon atoms which is different from the total number of carbon atoms of the most abundant two carbon numbers of olefins in the hydrocarbon stream.

3. The process as claimed in claim 2, wherein more than 10% by volume of olefin molecules in the hydrocarbon stream have a total number of carbon atoms which is different from the total number of carbon atoms of the most abundant two carbon numbers of olefins in the hydrocarbon stream.

4. The process as claimed in claim 3, wherein more than 20% by volume of olefin molecules in the hydrocarbon feed stream have a total number of carbon atoms which is different from the total number of carbon atoms of the most abundant two carbon numbers of olefins in the hydrocarbon stream.

5. The process as claimed in claim 1, wherein the hydrocarbon feed stream has an average number of carbon atoms per molecule of from 10 to 18.

6. The process as claimed in claim 1, wherein the hydrocarbon feed stream is derived from a Fischer-Tropsch condensate product.

7. The process as claimed in claim 1, wherein oxygenates are removed from the hydrocarbon feed stream prior to subjecting the stream to the hydroformylation reaction.

8. The process as claimed in claim 1, wherein the mid-boiling polar entrainer is Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, or Diethanolamine (DEA), or Diethylene glycol (DEG).

9. The process as claimed in claim 8, wherein the mid-boiling polar entrainer is DEG.

10. The process as claimed in claim 1, wherein the entrainer to feed ratio in the azeotropic distillation column is from 1:05 to 1:3.

11. The process as claimed in claim 10, wherein the entrainer to feed ratio in the azeotropic distillation column is from 1:1 to 1:2.

12. The process as claimed in claim 11, wherein the entrainer to feed ratio in the azeotropic distillation column is 1:1.8.

13. The process as claimed in claim 1, wherein said overhead stream from the azeotropic distillation column, containing paraffins and mid-boiling polar entrainer, is supplied to a decanter where a paraffin product is separated from the mid-boiling polar entrainer using a water wash.

14. The process as claimed in claim 13, wherein mid-boiling polar entrainer from the decanter is recycled to the azeotropic distillation column.

15. The process as claimed in claim 1, wherein said bottoms stream from the azeotropic distillation column is supplied to a wash column in which an alcohol/aldehyde product is separated from the mid-boiling entrainer using a water wash.

16. A method for separating alcohols/aldehydes from paraffins in a hydrocarbon feed stream in an azeotropic distillation column, wherein the solvent in the column is a mid-boiling polar entrainer, and wherein paraffins are recovered in an overhead stream, and alcohols/aldehydes are recovered in a bottoms stream from the azeotropic distillation column.

17. The method as claimed in claim 16, wherein the mid-boiling polar entrainer is Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, or Diethanolamine (DEA), or Diethylene glycol (DEG).

18. The method as claimed in claim 17, wherein the mid-boiling polar entrainer is DEG.

19. The method as claimed in claim 16, wherein the entrainer to feed ratio in the azeotropic distillation column is from 1:05 to 1:3.

20. The method as claimed in claim 19, wherein the entrainer to feed ratio in the azeotropic distillation column is from 1:1 to 1:2.

21. The method as claimed in claim 20, wherein the entrainer to feed ratio in the azeotropic distillation column is 1:1.8.

22. The process as claimed in claim 2, wherein more than 5% by volume of olefin molecules in the hydrocarbon stream have a total number of carbon atoms which is different from the total number of carbon atoms of the most abundant three carbon numbers of olefins in the hydrocarbon stream.

* * * * *